United States Patent [19]

Bruins et al.

[11] Patent Number: 4,547,327
[45] Date of Patent: Oct. 15, 1985

[54] METHOD FOR PRODUCING A POROUS PROSTHESIS

[75] Inventors: Paul F. Bruins, Brooklyn; Arthur Ashman, New York, both of N.Y.

[73] Assignee: Medical Biological Sciences, Inc., New York, N.Y.

[21] Appl. No.: 638,807

[22] Filed: Aug. 8, 1984

Related U.S. Application Data

[63] Continuation of Ser. No. 214,572, Dec. 8, 1980, abandoned.

[51] Int. Cl.$^4$ .................. A61C 13/00; A61C 13/08
[52] U.S. Cl. ..................................... 264/16; 264/19; 264/112; 264/126; 264/222
[58] Field of Search ............... 264/16, 126, 112, 19, 264/222

[56] References Cited

U.S. PATENT DOCUMENTS

| Re. 24,401 | 6/1972 | Wicherle et al. | 260/2.5 R |
|---|---|---|---|
| 3,446,875 | 5/1969 | Bruckmann et al. | 260/885 |
| 3,628,248 | 12/1971 | Kroder et al. | 32/10 A |
| 3,628,988 | 12/1971 | Stol et al. | 117/63 |
| 3,632,416 | 1/1972 | Shepherd et al. | 117/135 |
| 3,749,685 | 7/1973 | Johnson et al. | 260/2.5 M |
| 3,789,029 | 1/1974 | Hodosh | 260/2.5 R |
| 3,808,606 | 5/1974 | Tronzo | 3/1 |
| 3,882,858 | 5/1975 | Klemm | 128/92 |
| 3,906,550 | 9/1975 | Rostoker | 3/1.912 |
| 3,919,773 | 11/1975 | Freeman | 32/10 |
| 3,930,076 | 12/1975 | Kliment | 427/353 |
| 3,943,045 | 3/1976 | Cordrey et al. | 204/159.22 |
| 3,943,267 | 3/1976 | Randol | 427/2 |
| 3,971,134 | 7/1976 | Bokros | 32/10 |
| 3,992,725 | 11/1976 | Homsy | 3/1 |
| 4,051,598 | 10/1977 | Sneer | 32/10 |

(List continued on next page.)

FOREIGN PATENT DOCUMENTS

| 2255916 | 5/1974 | Fed. Rep. of Germany . | |
| 2449831 | 10/1974 | Fed. Rep. of Germany | 427/2 |
| 2105998 | 4/1972 | France . | |
| 2226160 | 10/1974 | France . | |

OTHER PUBLICATIONS

P. Boyne and D. Cooksel, J. Am. Dent. Assn., 71, 1426–1435 (1965).
K. Kliment et al., J. Biomed. Mater. Res., 2, 237–243 (1968).
B. S. Levowitz et al., Trans. Amer. Soc. Artif. Int. Organs, vol. XIV, 82–88 (1968).
G. D. Winter and B. J. Simpson, Nature, 223, 88–90 (Jul. 5, 1969).

(List continued on next page.)

Primary Examiner—Philip Anderson
Attorney, Agent, or Firm—Pennie & Edmonds

[57] ABSTRACT

A porous implantable oral prosthesis which can be used to replicate and replace any hard tissue portion of the mouth such as bone and teeth is described. The prosthesis comprises sintered polymeric particles coated with a hydrophilic material. The polymeric particles vary in size so as to provide an area of relatively coarse porosity where the prosthesis is intended to interface with bone tissue and relatively fine porosity where it is intended to interface with soft tissue. A process for producing such prosthesis by filling a mold with appropriate molding compounds comprised of polymeric particles and a hydrophilic monomer, sintering the particles and polymerizing the monomer by dielectric heating, removing the sintered material from the cooled mold, and placing the prosthesis in a hot liquid to remove residues is described. An entire tooth, including a nonporous crown may be produced. A process for producing a porous replica of a tooth root suitable for implantation immediately after extraction of a tooth is disclosed. When extraction has taken place in the past and has resulted in the bone and gum receding, a porous implant inserted in a newly drilled hole in the patient's jaw bone may be used. A central post associated with the implant projecting above the gum may be used for attaching a denture, partial bridge or a crown. A porous implant may be used for jaw bone replacement in order to improve the fitting of dentures.

19 Claims, 6 Drawing Figures

U.S. PATENT DOCUMENTS

| | | | |
|---|---|---|---|
| 4,093,576 | 6/1978 | deWijn | 260/17 |
| 4,118,532 | 10/1978 | Homsy | 428/294 |
| 4,131,597 | 12/1978 | Bluethgen | 260/42.18 |
| 4,164,794 | 8/1979 | Spector et al. | |
| 4,178,686 | 12/1979 | Riess et al. | 433/201 |
| 4,181,983 | 1/1980 | Kulkarni | 3/1 |
| 4,186,448 | 2/1980 | Brekke | 3/1 |
| 4,199,864 | 4/1980 | Ashman | 433/175 |
| 4,244,689 | 1/1981 | Ashman | 433/175 |
| 4,247,287 | 1/1981 | Gigante | 433/199 |
| 4,252,525 | 2/1981 | Child | 433/173 |
| 4,266,303 | 5/1981 | Park | 3/1.91 |
| 4,277,384 | 7/1984 | Arkens | 260/29.6 |
| 4,396,476 | 8/1983 | Roemer et al. | 204/159.16 |

OTHER PUBLICATIONS

G. D. Winter, *Proc. Roy. Soc. Med.*, 63, 1111-1115 (Nov. 1970).

J. S. Calnan, *Proc. Roy. Soc. Med.*, 63, 1115-1118 (Nov. 1970).

G. R. Taylor et al., *Journal of Surgical Research*, 11, 401-409 (Aug. 1971).

J. S. Calnan et al., *Brit. J. Plastic Surgery*, 24, 113-124 (1971).

S. Lerman and G. Sapp, *Canad. J. Ophthal.*, 6, 1-8 (1971).

L. Sprincl et al., *J. Biomed. Mater. Res.*, 4, 447-458 (1971).

M. F. Refojo, *J. Biomed. Mater. Res.*, 5, 113-119 (1971).

L. Sprincl et al., *Calc. Tiss. Res.*, 13, 63-72 (1973).

A. F. Hegyeli, *J. Biomed. Mater. Res.*, 7, 205-214 (1973).

S. D. Bruck, *J. Biomed. Mater. Res.*, 7, 387-404 (1973).

P. S. Walker et al., *Rheology of Biological Systems*, 260-277 (1973).

J. H. S. Simon and J. T. Kimura, *Oral Surgery*, 37, 936-945 (Jun. 1974).

P. Nathan et al., *Applied Microbiology*, 28, 465-468 (Sep. 1974).

M. Dumas and H. M. Myers, *Int. J. Oral Surg.*, 3, 273-277 (1974).

C. D. Metz et al., *J. Md. State Dental Assn.*, 17, 107-115 (1974).

R. H. Davis et al., *Proceedings of the Society for Experimental Biology and Medicine*, 147, 407-411 (1974).

J. A. Vale et al., *British Medical Journal*, 1, 5-9 (1975).

D. W. Rising et al., *Journal of Endodontics*, 1 (May 1975).

P. Nathan et al., *Infection and Immunity*, 12, 257-260 (Aug. 1975).

J. G. N. Swart et al., *Polymer Preprints*, 16, 368-371 (Aug. 1975).

R. A. Abrahams and S. H. Ronel, *American Chemical Society Polymer Preprints*, 16, 535-540 (1975).

R. M. Rubin and J. L. Marshall, *J. Biomed. Mater. Res.*, 9, 375-380 (1975).

Z. Voldrich et al., *J. Biomed. Mater. Res.*, 9, 675-685 (1975).

D. G. Murray and J. S. Dow, *J. Biomed. Mater. Res.*, 9, 699-707 (1975).

B. M. Libin et al., *Journal of Periodontology*, 46, 51-56 (1975).

*Journal of the American Medical Association*, 236, 335-336 (Jul. 26, 1976).

B. H. Benkel et al., *Journal of Endodontics*, 2, 196-202 (Jul. 1976).

J. T. Mellonig et al., *Journal of Periodontology*, 46, 125-131 (1976).

P. Nathan et al., *Trans. Amer. Soc. Artif. Int. Organs*, vol. XXII (1976).

P. Nathan et al., *American Burn Association, Ninth Annual Meeting*, (Mar. 31-Apr. 2, 1977).

J. J. Klawitter et al., *J. Dent. Res.*, 56, 385-393 (Apr. 1977).

J. Henahan, *Medical Tribune*,(May 11, 1977).

A. Ashman and M. L. Moss, *J. Prosthet. Dent.*, 37, 657-665 (Jun. 1977).

J. H. Kronman et al., *J. Dent. Res.*, 56, 795-801 (Jul. 1977).

B. V. Rejda et al., *ESAO II*, 62-67 (1977).

K. Robinson et al., *IADR Abstracts*, 379 (1978).

R. Green et al., *IADR Abstracts*, 380 (1978).

L. J. Peterson et al., *J. Dent. Res.*, 58, 489-496 (Jan. 1979).

L. B. Goldman et al., *Quintessence International* 2/1979, 101-107 (Feb. 1979).

J. H. Kronman et al., *Oral Surgery, Oral Medicine, Oral Pathology*, 48, 175-177 (Aug. 1979).

H. W. Denissen and K. de Groot, *The Journal of Prosthetic Dentistry*, 42, 551-556 (Nov. 1979).

H. G. Willert et al., *Arch. Orthop. Traumat. Surg.*, 94, 265-292 (1979).

A. Harrison et al., *J. Biomed. Mat. Res.*, 13, 23-34 (1979).

L. L. Hench, *Science*, 208, 826-831 (May 23, 1980).

H. W. Denissen et al., *Clinical Preventive Dentistry*, 2, 23-28 (Jul.-Aug. 1980).

METHOD FOR PRODUCING A POROUS PROSTHESIS

This is a continuation of application Ser. No. 214,572 filed Dec. 8, 1980 now abandoned.

FIELD OF THE INVENTION

This invention relates to an oral prosthesis and the process for producing it. More particularly it relates to porous implants which allow for the growth of bone and gum tissue into the implant to assure that it is firmly attached to the body structures and becomes an integral part or fixation thereof. It further relates to molding compounds for such implants. It also relates to a process for rapidly molding such implants to replace the root of an extracted tooth, an entire tooth or a section of bone with an identically shaped replica within a short period of time after extraction or during a single office visit.

BACKGROUND ART

Oral prosthetic devices, in the form of dental implants are one class of biologically compatible components used in the body to replace injured or diseased body structures. Such components are biologically compatible in the sense that implantation of such devices has no adverse effect upon the living tissue, and the environment of the body does not adversely affect the device. It may be necessary to replace entire bony structures, fill bone defects, or replace extracted teeth.

The replacement of a bone section or a tooth offers the particularly challenging problem of finding a biologically compatible material which will allow tissue growth to penetrate into the material.

U.S. Pat. No. 4,186,448 to Brekke discloses a device and method for treating a newly created bone void or soft tissue deficiency. A body made of a biodegradable material, such as polylactic acid, including enclosed interconnected randomly positioned, randomly shaped and randomly sized voids extending throughout the mass of the body attracts blood by capillary action, leading to healing of the bone void as the body member biodegrades and is absorbed by the tissue. A wetting agent such as sodium oleate or Ultrawet 60 L (T.M.) sold by the Fisher Scientific Company of Chicago, Ill. assists the capillary action (See Column 1, lines 55-62). This type of implant, while promoting healing and possibly preventing the bone structure around an extracted tooth from receding, does not provide a structure to which replacement crowns for extracted teeth can be attached.

"Fabrication and Characterization of Porous-rooted Polymethylmethacrylate (PMMA) Dental Implants," by Klawitter et al. published in the *Journal of Dental Research*, April 1977, p. 385 discloses polymethylmethacrylate dental implants having a porous coating on the root portions. The coating is developed by adding methylmethacrylate monomer to polymethylmethacrylate beads to soften the surface of the beads, and then compression molding the mixture at high pressure. Pore sizes of 20-40 micron diameter are indicated as being restrictive of bone growth but allowing for fibrous tissue ingrowth, while those of approximately 200 micron diameter are disclosed as appearing to be optimum for bone tissue ingrowth.

U.S. Pat. No. 4,199,864 to Ashman discloses a method for fabricating polymeric plastic implants for endosteal or periosteal applications having a porous surface with pores of a predetermined size, pore depth, and degree of porosity. Leachable substances, such as sodium chloride crystals of controlled particle size are added to a powdered polymer-liquid monomer mixture in relative amounts corresponding to the desired degree of porosity. These crystals, combined with mold release agents, are used to coat mold cavity surfaces to achieve proper near-surface porosity. After heat polymerization without the use of an initiator, and abrasive removal of resulting surface skin, the salt is removed by leaching to provide the desired porosity. Bone ingrowth is promoted by pore sizes in the 200-400 micron range. Pore sizes of 50-150 microns result in soft tissue in growth. The use of two different size pores in a single implant is disclosed at column 3, lines 29-36.

DISCLOSURE OF THE INVENTION

The present invention provides an oral prosthesis comprised of a porous biologically compatible material. Unlike the Brekke patent cited above the implants of the present invention are made of a nonbiodegradable material, have specific pore sizes per unit area, which are not randomly spaced throughout and require no wetting agent. A molding compound comprised of particles of the material, which is preferably a biologically compatible polymeric plastic, such as polymethylmethacrylate (PMMA), is combined with a monomeric hydrophilic material which physically coats the particles, and is polymerized while sintering in a dielectric oven. The PMMA may be of a modified form including a plasticizer or a comonomer. The polymerized hydrophilic material facilitates the infusion of body fluids into the implant, which is coarsely porous where it must interface with bone tissue, and finely porous where it must interface with gum tissue.

The hydrophilic material is advantageously a lightly inhibited monomer, such as hydroxyethylmethacrylate (HEMA) which physically coats, but does not chemically interact with, the polymeric material. Heating provides sufficient free radical activity to overcome the effect of the inhibitor, resulting in polymerization of the coating and the bridges between the particles during sintering, thus assuring adequate strength. Post sintering immersion for a brief interval in boiling water sterilizes the implant and removes residual monomer and inhibitor. Thus, the final step in the process of producing the implant renders is sterile.

The hydrophilic coatings swell but do not generally dissolve in body fluids. In order to assure that dissolution is prevented, a small quantity of cross-linking agent may be added to the polymer-monomer mixture, thus increasing the effective molecular weight of the polymerized hydrophilic material.

When a tooth is extracted it is desirable to fill the void created to prevent recession of the gum and bone. It is necessary, if a replacement crown is to be provided, to have a root implant to which the crown can be fastened, and which will adequately support the crown. Further, for best results and strong attachment to bone and gum tissues, the implant should be placed in the extraction cavity almost immediately after extraction. It should be of the same size and shape as the root of the extracted tooth, or possibly just slightly larger in size to fit snugly into the cavity.

The present invention provides a method of fabricating a replica of the root of the extracted tooth within a very short time after extraction, allowing the root implant to be inserted into the extraction cavity during the same office visit as the extraction. Using the cleaned, extracted tooth, a mold is produced which is a replica of the root section of the tooth. It is filled by packing with molding compounds comprised of different sizes of polymer particles to provide the two required sizes of pores. Sintering is accomplished in minutes by heating in a dielectric oven. After cooling, removal from the mold and immersion in a hot liquid to remove impurities, the implant is cut down in size so it may be completely enclosed and covered by the patient's gum tissue (except for possibly a part protruding through the gum) where it remains for several weeks or months to allow the ingrowth of bone and gum tissue before a crown is mounted.

To produce a snugly fitting root implant the cleaned, extracted tooth is immersed in molten wax and withdrawn, allowing a thin conformal coating of wax to solidify on the root. A replica produced by using this wax coated tooth root will be of the proper shape but slightly larger than the original root. This will not affect the ability to insert the replica as there is some latitude in the size of an implant which the bone and tissue can accept.

A prefabricated denture tooth such as that made by denture manufacturers may be attached to an implanted root made by the present invention or the process of the present invention can be used to produce an entire tooth when necessary or desirable. To do so it is necessary to prepare a mold of the crown, or upper portion of the tooth, as well as the root portion. The extracted tooth which is to be replicated remains in a mold of the type described above. This mold, with the tooth in place, is used to produce a mating mold having a cavity in the shape of the crown. After the molds have been disassembled and the patient's tooth removed, a porous root is then produced in the root mold by the process described above. The second mold cavity is filled with a material such as a fast setting polymer formulation which polymerizes to form an artificial crown. As soon as this crown mold cavity of the mating mold is so filled, the root mold, with the porous sintered root in place in its mold cavity is placed in proper alignment above and the crown mold. Penetration of the liquid into the porous root occurs as the liquid sets. Air pressure may be used to prevent the formation of voids during the cure of the polymer formulation. A post cure in a dielectric oven may be utilized to assure completion of polymerization. After cooling the molds are disassembled from one another, and the complete artificial tooth removed. Mold parting line flash is removed from the tooth, which is then immersed in boiling water to remove impurities. The complete tooth can then be secured in the cavity in the mouth by attachment to adjacent teeth by acid-etch and "bonding" techniques, while tissue grows into the root portion.

Where bone and gum tissue have receded due to prior extractions an anchor for partial dentures or a bridge which may be implanted can be fabricated by drilling a conical cavity in the patient's jaw bone, making an impression of this cavity, using the impression to generate a mold, and then using this mold to produce a porous article of the shape of the conical cavity following the procedure outlined above for producing a tooth root. This anchor is provided with a central post projecting above the gum line to which a partial denture, a bridge or a crown may be attached.

DETAILED DESCRIPTION OF THE INVENTION

Figure 1:
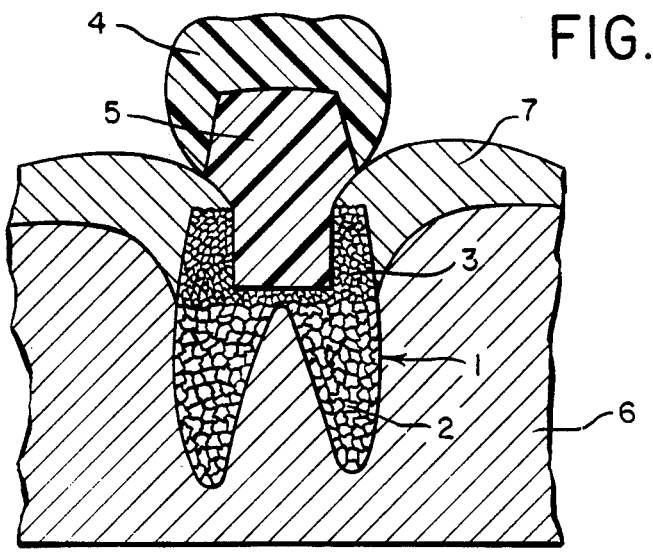
FIG. 1 is an enlarged cross sectional, side elevation of a crown and a tooth root made in accordance with the invention showing the pores in greatly enlarged scale.

This invention may be used to produce a variety of oral prostheses. Various types are disclosed and illustrated in U.S. Pat. No. 4,199,864 for "Endosseous Plastic Implant Method" to Ashman.

A prosthesis may be produced by molding to predetermined sizes and shapes to fit a particular patient. The cavity of an appropriate mold is packed initially with coarse polymeric particles, which are coated with a hydrophilic material. In the process of the invention it is only necessary to pack the material utilizing strong manual pressure. A quantity of this material sufficient to form a portion of the implant which will interface with bone tissue is utilized leaving a portion of the mold cavity unfilled. This remaining volume is packed in a similar fashion with fine polymeric particles which are coated with a hydrophilic material, forming a portion of the implant which will interface with gum tissue. The packed mold is heated at atmospheric pressure in a dielectric oven where sintering of the PMMA and polymerization of the HEMA in the mold cavity occurs. After the mold has cooled, aided by immersion in cold water, the sintered prosthesis is removed from the mold and immersed in a hot liquid for a short period of time.

Occasionally it is desirable to produce an implant which is an exact replica of a patient's whole tooth. If an exact replica can be inserted into the cavity formed when a diseased tooth is extracted, within a short time after extraction, i.e. within the same office visit, ingrowth of bone and gum tissue is facilitated and the implant will become an integral part of the tissue structure. An implant of this variety may be produced by the process outlined below if the extracted tooth is cleaned and used to form a mold comprised of a rapidly setting material. Setting of the mold may be accelerated by dielectric heating. The mold is formed in a matter of minutes and may then be packed, as described above, the material sintered, and a replica of an extracted tooth root produced according to the invention within a period of approximately fifteen minutes to one half hour.

A mold for the upper portion of the tooth is prepared after the mold for the root portion has been made, with the patient's extracted tooth as the pattern, in place in the root mold. A parting agent, such as petroleum jelly is used to coat the top surface of the root mold. Then the rapid setting mold material is used to make a replica of the upper crown portion of the patient's tooth. After cure, (requiring two minutes of dielectric heating) the upper and root portions of the mold are separated. After the porous root portion of the tooth is made, as described above, the crown portion of the mold is filled with a non-porous, fast setting methylmethacrylate (MMA) formulation containing PMMA particles, pigment, filler, catalyst and promoter, mixed with monomeric MMA, a conventional formulation commercially available. While this mixture is still liquid in the crown mold, the root portion of the mold, containing the sintered porous root, is placed on top of the crown mold in perfect alignment, so that the sintered root, with or without a center post of PMMA, contacts the liquid mixture in the crown mold. The liquid portion is converted to solid PMMA, with or without additional dielectric heating. When the root and crown molds are separated, a replica of the patient's tooth, having a porous root and non-porous crown may be removed from the mold, ready to be inserted into the patient's cavity. Total elapsed time is less than one hour.

Any prosthetic device produced according to this invention may be reinforced by inserting a solid polymer core, such as PMMA into the material packed within the mold cavity.

As indicated above, the dental implants of this invention are produced from materials which can be implanted in living body tissue without adverse effect on the body or the implant. The materials must be easily molded to a particular size and configuration, appropriate for the individual need of a dental patient. The molded implant must have adequate strength to withstand the loads of normal use and occasional abuse. The materials should also be low in cost and readily available. Recent developments in the science of biologically compatible materials have resulted in larger numbers of materials which meet these requirements and more materials are being accepted for use within the body.

A class of materials which has been accepted for use in body tissue for many years is the acrylics. Of these, the material with some of the best mechanical properties is polymethylmethacrylate (PMMA). While it will be understood that the present invention may be practiced by using a variety of base materials, the discussion will be restricted to the use of PMMA. The sintering of PMMA particles to produce a porous implant is not broadly new. Such a structure, however, is often not readily penetrated by body fluids due to the hydrophobic nature of untreated PMMA particles.

A highly effective method of assuring adequate penetration, and therefore sufficient ingrowth of body tissue, an important feature of this invention, is the coating of the PMMA particles with a hydrophilic material. While many hydrophilic materials could conceivably be used, it has been found that polyhydroxyethylmethacrylate (PHEMA) is an excellent coating. Because of its hydrophilic nature, it will swell on exposure to body fluids but will not generally dissolve in these fluids.

The preferred method for obtaining a PHEMA coating on the PMMA particles is to use HEMA monomer to wet the PMMA particles just prior to packing the mold. A mixture of approximately ten percent by weight HEMA and ninety per cent PMMA is the optimum mix ratio. This ratio may be varied however from approximately five percent to twenty percent, a slight excess of HEMA being preferred if the optimum ratio is not used. The combining of these ingredients to form a molding compound is preferably and most conveniently carried on at room temperature but could be carried on at any temperature in the range of 5° C. to 35° C.

The HEMA monomer, in liquid form at room temperature, should be lightly inhibited from polymerizing by trace amounts of an inhibitor such as the methyl ether of hydroquinone (MEHQ). This should be present in a concentration in the range of 150 to 300 parts per million and, preferably, 200 parts per million. It has been found unnecessary to add any material to neutralize the inhibitor to allow polymerization of the HEMA. Raising the temperature during the sintering process provides sufficient free radicals to allow polymerization to occur.

The polymerized HEMA coating will physically bond to the PMMA particles but will not chemically react with the PMMA. This bond is sufficiently strong to aid in preventing physical breakdown of the sintered structure. To further assure against dissolution of the coating, a cross linking agent comprising a methacrylic diester of ethyleneglycol may be added to the inhibited HEMA-PMMA mixture to increase the effective molecular weight of the polymerized HEMA coating. This cross linking agent may comprise one tenth percent to five percent by weight of the HEMA monomer. It is preferably triethyleneglycol dimethacrylate or alternatively tetraethyleneglycol dimethacrylate. Diethyleneglycol dimethacrylate and monoethyleneglycol dimethacrylate may also be used. Combinations of these four diesters with a combined weight from one tenth percent to five percent of the HEMA may be used. HEMA monomer usually contains a small amount (1% or less) of monoethyleneglycol dimethacrylate initially, unless specially purified, because this diester forms spontaneously in HEMA by the process of transesterification.

After two or three minutes of mixing the inhibited HEMA-PMMA mixture, with or without a cross linking agent, the PMMA particles become tacky annd the HEMA physically penetrates into the PMMA surface, resulting in an excellent welding action during subsequent sintering, which produces a stronger implant than one resulting from the sintering of only PMMA particles. Where the HEMA coated particle surfaces meet, the polymerization and cross linking of the HEMA, which is chemical in nature, contributes to this result, producing a porous implant of exceptional strength.

The size of the pores may be controlled by the size of the PMMA particles used. It is generally convenient to use commercially available beads of 40 to 60 mesh, which correspond to a particle diameter of about 250 to 420 microns, to produce pore sizes of 125 to 210 microns, which are suitable for soft tissue ingrowth. Beads of 20 to 24 mesh, corresponding to particle diameters of approximately 700 to 840 microns, produce pore sizes of 350 to 415 microns, which are suitable for bone ingrowth. Such PMMA beads are made by suspension polymerization and are spherical in shape. They are made by Esschem Co. of Essington, Pa. and are called Polymer Type 5, which indicates that they are comprised of five percent dibutyl phthalate.

To produce a dental implant having a portion designed to interface with bone or hard tissue including large or coarse pores, and a portion designed to interface with gum or soft tissues having small or fine pores, as defined above, it is necessary to pack a mold of the described dental implant with molding compounds produced with PMMA particles of the above indicated sizes. For example, generally the lower portion of the mold, as in the case of a root implant, will produce that part of the implant which will interface with bone tissue. The mold is thus packed with a molding mixture as described above containing PMMA particles in the diameter range of 700 to 840 microns. A sufficient quantity of material is used to fill the mold to the point at which the material which is tamped in by using manual pressure fills the portion of the implant which will be associated with bone tissue where ingrowth and adhesion of periodontal membrane tissue is desirable. The remaining portion of the mold is then filled with a molding compound as described above, having PMMA particle diameters in the range of 250 to 420 microns suitable for soft tissue ingrowth. This material is also tamped in by hand.

The molds into which the molding compound is packed may be of any type known in the prior art which will withstand the stress of manual tamping without undue deformation and will not be adversely affected by exposure to temperatures necessary to sinter the molding compound. Under certain circumstances it may be necessary to spray the surface with a release agent but this is generally not necessary with the preferred molding materials. The preferred material for the mold, which sets rapidly, especially when dielectrically heated, is Citricon silicon putty mixed with Citricon catalyst both well known and manufactured by the Kerr Dental Products Division of Sybron located in Romulus, Mich. The procedure for using this material is described below.

The material packed in the mold is sintered by heating in a dielectric oven such as a Model E0-1 manufactured by W. T. Rose and Associates of Troy, N.Y. at a temperature in the range of 150° C. to 225° C. for three to six minutes, but preferably four minutes. The oven's upper electrode is adjusted to provide one quarter inch clearance between it and the top of the mold. Temperatures in this range create enough free radicals to overcome the effect of the inhibitor in the HEMA monomer, resulting in polymerization of the physically bonded HEMA coatings and HEMA bridges between the PMMA particles where they are in contact with one another. Cross linking also occurs when an appropriate cross linking agent, as specified above, is used.

After sintering the mold is removed from the dielectric oven and cooled by partial immersion in water. The cooling is allowed to progress until the implant gains sufficient strength to allow it to be removed from the mold without damage. The mold may be split to facilitate removal.

The resulting implant will generally contain unreacted HEMA monomer or, possibly, exceedingly small amounts of inhibitor. These materials may be removed by immersion of the implant in a hot liquid which will leach out the residue without damaging the implant or leaving behind components of its own. Immersion of the implant in boiling water for one and one-half to two and one half minutes is usually adequate.

The portion of the volume of the finished implant which constitutes the pore volume is advantageously approximately thirty percent and is preferably uniformly distributed, but it may be between twenty percent and forty percent. Lower percentage porosity will not allow adequate infusion of body fluids necessary for tissue ingrowth, and higher percentages of porosity will decrease the strength of the implant.

It is desirable to implant a replacement tooth root which is a replica of the extracted tooth root before the gum and bone tissue can recede away from the extraction site. This promotes rapid healing of the area, a firm bond between the body tissue and the implant, and helps reduce the possibility of a rejection of the implant by the tissue. The present invention can be utilized to produce such a replica, which has coarse porosity where it fits within the jawbone socket interfacing with hard tissue. In such areas the ingrowth or adhesion of bone or periodontal membrane tissue is necessary. In areas which interface with soft gum tissue, finer porosity is advantageously utilized to produce tissue ingrowth.

A method for utilizing the present invention to make a replica of the root of the extracted tooth is set out below. This procedure leads to the production of a replica within approximately twenty minutes of tooth extraction. Thus the implant may be inserted in the patient during the office visit in which the tooth is extracted.

EXAMPLE 1

Procedure for replacement of a newly extracted tooth by an implantable root.

A tooth root may be rapidly molded by following the steps outlined below:

(1) The tooth is extracted and cleaned of tissue material not part of the tooth. (Elapsed Time—1 minute)

(2) Twenty-five grams "Citricon" silicone putty is mixed with ten drops "Citricon" catalyst for one minute and pressed into a polyethylene ring, one inch in inner diameter by one inch high on a glass plate. The mixture is packed well to eliminate voids and excess material is trimmed. (Elapsed Time—1.5 minutes)

(3) The extracted tooth is pressed into the silicone putty up to and slightly beyond the point representing the gum line. The resulting mold is placed in a dielectric heating oven. The upper electrode is adjusted to be one quarter inch above the top of the tooth. The mold material is dielectrically heated for two minutes. The tooth is removed from the mold with a rocking motion. (Elapsed time—3 minutes)

(4) In a small beaker 0.4 gms of 20 to 24 mesh acrylic (PMMA) beads are thoroughly mixed with 2 drops (0.04 gms) of HEMA (hydroxyethylmethacrylate mixed with 1% of triethyleneglycol dimethacrylate). In another small beaker 0.6 gms of 40 to 60 mesh acrylic beads are thoroughly mixed with 3 drops (0.06 grams) of HEMA (also containing the triethyleneglycol dimethacrylate) for one minute. This may be done while the silicone mold is heating and curing. (Elapsed time—1 minute)

(5) The lower part of the silicone mold cavity is filled with the 20 to 24 mesh mixture, forcing it down, with a spatula, into the root channels to fill to about ⅓ to ½ of cavity depth. The walls of the cavity above this point are cleared of the 20 to 24 mesh particles. (Elapsed time—1 minute)

(6) The remainder of the mold cavity is filled with the 40 to 60 mesh mixture. The material in the mold is pressed down as hard as possible by hand, using a polyethylene film to avoid hand contact. The filled cavity should be level with the top of the mold. Excess is trimmed away. (Elapsed time—2 minutes).

(7) The filled mold is placed in a dielectric oven, with the upper electrode adjusted to be one quarter inch above the top of the mold. Heat is applied for four minutes. The mold is removed and cooled by semi-immersion in water for 2 minutes. (Elapsed time—6 minutes)

(8) The silicone mold is removed from the polyethylene sleeve, which is reuseable. The molded tooth root is gently pried out so as not to damage the long curved root ends, or the mold may be split to remove a complexly shaped root after making sure that the root is cool enough to be strong. (Elapsed time—2 minutes)

(9) The tooth is placed in boiling water for two minutes to extract any residual monomer and inhibitor. (Elapsed time—2 minutes)

(10) The top of the root is trimmed to the desired height so that when inserted in a patient's cavity it can be completely enclosed and covered by the patient's gum tissue. (Elapsed time—2 minutes).

Total elapsed time is equal to 21.5 minutes.

It is also possible to make the porous root slightly larger than the removed tooth root for a tighter fit. Dipping the extracted tooth in a molten wax, in order to coat it uniformly, and allowing it to solidify enlarges all dimensions slightly.

After the bone and tissue have become attached (estimated to take 2-6 weeks) the dentist can attach the upper part of the tooth or crown by conventional means after making the necessary incision in the gum to reach the implant or prosthesis. The shape and position of the crown may be duplicated by means of an impression taken prior to the extraction.

In order to facilitate attachment of the crown to the implanted root it is often desirable to provide a temporary, centered rod or post in the porous root. This post may be made of high density polyethylene or polypropylene or other non-polar plastics, of one sixteenth to one eight inch in diameter, depending upon the size of the root implant. The lower portion of the post may be threaded to facilitate subsequent removal. This post is inserted into the packed porous implant prior to sintering as in step No. 7 of Example 1. Because it is non-polar, it does not become heated in the dielectric field and it does not become bonded to the sintered PMMA particles.

Prior or subsequent to insertion of the sintered root implant in the patient's tooth cavity, the height of the post is adjusted by trimming, so that the top of the post is at the same level as or protruding slightly above the top of the gum, and the gum is sutured around the post, so that only the top of the post is visible or slightly protruding.

After the bone and tissue have become attached, the dentist can now readily locate the exact position of the implant, and remove the temporary post by unscrewing it, without disturbing the implant. The resulting hole in the implant is now used to insert a PMMA non-porous post or shaped post as shown in FIG. 1. The PMMA post need not be threaded. It can be firmly attached to the implant by means of a fast setting acrylic or cyanoacrylic adhesive.

Referring to FIG. 1, there is illustrated an implantable root 1, showing an area of coarse porosity 2 which interfaces with bone 6, and an area of fine porosity 3 which interfaces with gum tissue 7. A post 5 is provided as a means of strengthening root 1 and mounting a crown 4, by the use of a suitable adhesive well known in the art. It is understood that the porosity extends throughout the entire root, and that the entire surface is porous. Post 5 is formed from a solid acrylic (PMMA) and may be inserted in the mold prior to sintering, immediately thereafter, or after the removal of the temporary non-polar post. It may be formed from a rod or a shaped post having a base one sixteenth to one eighth inch in diameter depending on the size of the patient's tooth.

Figure 2:
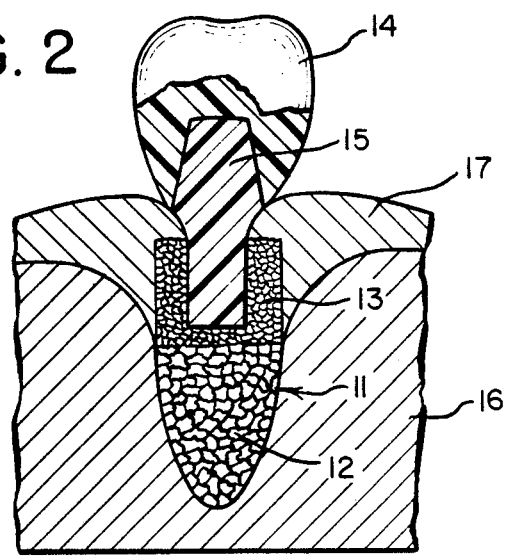
FIG. 2 is an enlarged cross sectional side elevation of a porous implant made in accordance with the invention attached to a crown by means of a post.

FIG. 2 illustrates a replacement structure 11 for a smaller tooth, with possibly a less complex root structure. Areas of coarse porosity 12 which interfaces with bone 16 and fine porosity 13 which interface with gum tissue 17 are shown. Crown 14 is attached to root implant 11 by means of post 15 which has a base one sixteenth inch in diameter.

Figure 3:
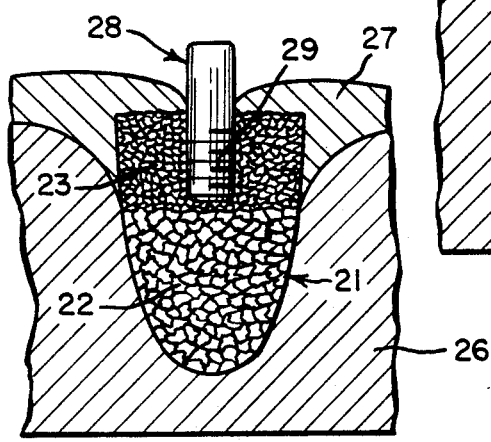
FIG. 3 is an enlarged cross sectional view of a porous implant including a temporary post made from a nonpolar plastic.

FIG. 3 illustrates an implantable root 21 with an area of coarse porosity 22 which interfaces with bone 26 and fine porosity 23 which interfaces with gum tissue 27. Root 21 is made with a temporary post 28 of a non-polar plastic which is readily removable from the root by means of thread 29 in order to subsequently replace it with a PMMA post.

A method of utilizing the present invention to make a replica of the entire extracted tooth is set out below. This procedure leads to the production of a replica of the entire tooth within one hour or less. Thus the complete replacement of the patient's extracted tooth can be accomplished during the office visit in which the tooth is extracted.

EXAMPLE 2

Procedure for replacement of a newly extracted tooth by an implantable tooth.

(1) The patient's extracted tooth is inserted in the root mold previously made by the procedure described in Example 1. The top surface of the mold should be flat and at a position corresponding to the gum line of the tooth. Notches are cut into the top surface in order to later align the mold of the crown with the root mold. The root mold is inserted in the original polyethylene ring in which it was previously made.

(2) The top surface of the root mold is coated with a thin layer of petroleum jelly or similar lubricant which acts as a parting agent.

(3) A second polyethylene ring of the same diameter is placed on top of the root mold ring, the second ring having a height equal to the height of the patient's tooth projecting above the root mold surface, plus an additional one quarter of an inch.

(4) Sufficient "Citricon" silicon putty and "Citricon" catalyst, are mixed (for example twelve and one half grams of putty and 5 drops of catalyst), for one minute, and pressed into the upper polyethylene ring, filling the ring completely. The ring is packed well to eliminate voids, and excess material is trimmed. The molds are heated dielectrically for two minutes, with the top electrode of the dielectric oven one quarter inch above the top of the molds, to complete the cure of the silicone mold. The molds are then cooled for one minute by immersion in water. The top and bottom molds are separated and the patient's tooth removed.

(5) The crown mold is now filled with a fast setting MMA liquid formulation consisting of PMMA powder blended with pigment, filler, catalyst, promoter and monomeric MMA, lightly inhibited, which is usually proportioned to be two parts powder to one part monomer. This mixture of powder and liquid is blended and mixed for thirty seconds and then used to fill the crown mold. The above described formulation is commercially available in various tooth color shades, for example, "Jet Acrylic" manufactured by Lang Dental Mfg. of Chicago, Ill. or "Super-C" manufactured by Amco, Inc. of Philadelphia, Pa. Such formulations complete the hardening reaction at room temperature (70° F.) in about five minutes.

(6) As soon as the crown portion of the mold is filled with the above liquid mixture, the root mold, with the porous sintered root inserted in place, and made by the previously described procedure, is placed above the crown mold, using the molded in notches for perfect alignment. The root mold contacts and absorbs some of the liquid mixture in the crown mold. As the porous root contacts the liquid mixture, the excess liquid mixture is squeezed out at the parting line. A clamp is used to hold the two molds together while the liquid mixture is hardening.

Optionally, the porous sintered root may have a center post of a solid polymer core preferably made of PMMA, which is bonded to the porous sintered root, and projects into the liquid mixture. The monomeric MMA in the liquid mixture softens the PMMA post surface and then polymerizes, thus forming a strong bond.

Optionally, as soon as the two molds are joined and clamped, the assembly may be placed in a pressure vessel, and the pressure raised by means of a compressed fluid, such as air, to 60 psi or more while the liquid mixture is converting to a solid. The purpose of this additional pressure is to reduce or completely prevent formation of any voids in the crown portion of the tooth caused by vaporization of monomer due to the exothermic heat of the polymerization reaction.

(7) The crown and root portions of the molds are separated, and the completed replica of the patient's tooth removed from the mold. Any "flash" or excess hardened material at the interface is removed, and the crown surfaces may be buffed and polished.

(8) The complete finished tooth is placed in boiling water for two minutes to remove residual monomer or inhibitor from the porous root portion. This is done only after the entire tooth is made.

(9) The replica of the patient's tooth is inserted into the cavity formed by the extraction in the patient's mouth. It must remain immobile in order to permit bone and tissue attachment. This may be accomplished by several means, for example, wire attachment to adjacent teeth. When a visible front tooth is replaced, a less noticeable form of attachment may be used. For example, a fast setting transparent adhesive such as "Cyanodent" made by the Ellman Dental Laboratories of Hewlett, N.Y. may be used. This material is made with a cyanoacrylic monomer similar to Eastman 910, made by Eastman Kodak, and is well known for its use as an adhesive.

Where teeth have been extracted for some time and the bone and gum tissue have receded, a region known as the "edentulous" area forms and there is a need to create an anchor for partial dentures or a bridge. Such an anchor can be provided in the form of an implant which attaches to the bone and tissue and is produced by the following procedure:

EXAMPLE 3

Procedure for producing an implantable root or entire tooth when the bone and gum have receded due to extraction at some previous time.

(1) The gum is cut open at the site for the implant and a conically shaped hole drilled in the bone, using progressively larger shaped drills adapted for use with a dental drill. The finished hole should be about one quarter inch in diameter at the bone surface, and tapered, with a total depth bringing it no closer than two millimeters from a nerve. The position of the nerve is determined by well known x-ray techniques.

(2) An impression of the drilled hole is made, using a fast setting, very low shrinkage acrylic formulation, such as "Duralay" made by Reliance Dental Mfg. Co. of Worth, Ill. This impression is used as a model to make a "Citricon" silicone mold.

(3) The porous implantable root is then made as described in Example 1, or a whole tooth is made as in Example 2 using the silicon mold to reproduce the shape of the drilled hole. That portion of the root in contact with bone is made having a pore size of 350 to 415 microns, while the portion in contact with gum tissue is made having a pore size of 125 to 210 microns.

(4) The implant is placed in the prepared bone socket, and the gum tissue is sutured around the temporary or permanent post. The implant is then left undisturbed for two to six weeks until bone and tissue attachment has occurred. If the post is the temporary type, it is removed and replaced with a PMMA post preferably of the conical type show in FIG. 1

(5) The conical projecting portion of the post is then used for attaching the crown portion, or a bridge. The crown is a molded tooth having a socket which conforms to the shape of the conical post and is cemented in place using fast setting acrylic adhesive.

While the invention has been described as using polymethylmethacrylate particles coated with hydroxyethylmethacrylate, it is understood that other biologically suitable materials may become available for use with the present invention.

When an implant produced according to the present invention is placed in a cavity in a patient's jaw it is desirable that it be possible to obtain meaningful data on progress as time goes on by the use of X-ray techniques. The HEMA coated PMMA of the implant will not generally have an X-ray density sufficient to provide meaningful contrast on X-ray film. A radio-opaque material such as barium sulfate may be incorporated into the mixture used to make the molding compounds used in the invention and will therefore be dispensed throughout the prosthesis. for example 0.7 micron barium sulfate particles comprising one to five percent by weight of the PMMA beads can be blended with the PMMA beads used in the process of the invention. These particles will coat the PMMA beads, producing an implant which has a sufficient X-ray density to produce a clear image on an X-ray film.

Figure 4:
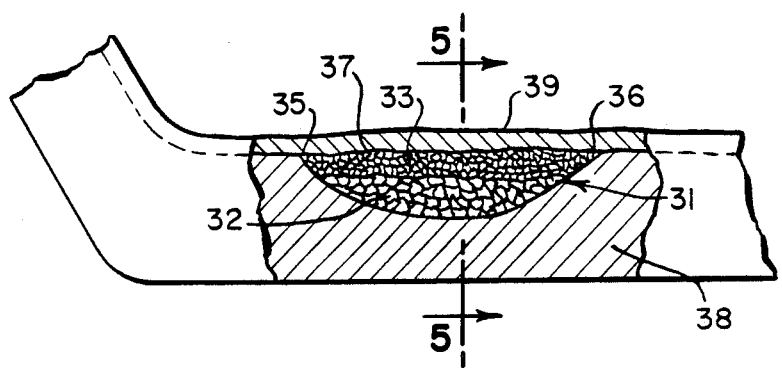
FIG. 4 is a side elevation in partial cross sectional of a jaw bone implant made according to the invention.
Figure 4A:
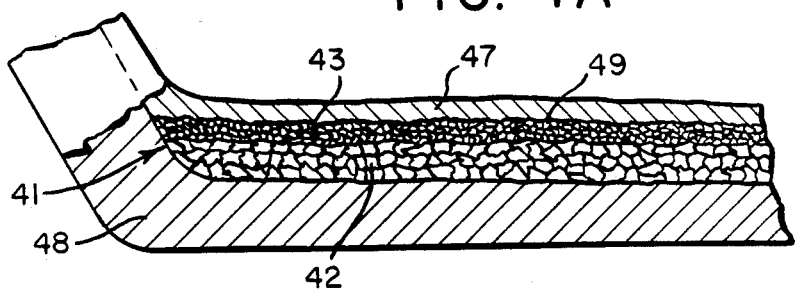
FIG. 4A is a cross sectional side elevation of a jaw bone implant used when a larger region of bone has deteriorated.

An implant according to the present invention may also be used to replace a missing section of jaw bone where deterioration has taken place, as shown in FIGS. 4 and 4A. Referring to FIG. 4 an implant 31 having a region of coarse porosity 32 which interfaces with bone 38 and a region of fine porosity 33 which interfaces with gum tissue 39 may be produced by surgically opening the gum, taking an impression of jaw bone 38, and producing a mold. The impression may be shaped so that the implant smoothly fits with the existing jaw bone at its ends 35 and 36 and follows the contour or surface 37 that a jaw without signs of deterioration would have.

In addition, implants produced according to the present invention can be used to build up edentulous ridges in patients with dentures. The building up of the vertical height of these ridges can augment the natural ridges of the jaw bone which exist when the teeth have been removed, preventing denture movement such as rocking and sliding. Such ridges may be incorporated on surface 37 of implant 31 of FIG. 4, or similarly on the implant of FIG. 4A. Alternatively such ridges may be formed by separate small implants on a jaw which has suffered less deterioration.

EXAMPLE 4

Procedure for producing jaw bone implantable additions for improved denture fitting.

In cases where the bone has receded due to long prior tooth extractions, the gum is surgically opened along the line of the jaw bone and an impression is taken of the shape of the bone using Citricon silicone mold material. This mold is used to cast or manufacture a so-called Stone model (a hard plastic for dental use, well known in the art) by pouring Stone into the Citricon mold. Then the height of the resultant model is increased by adding hard wax or fast setting plastic to the cast until the model has increased in thickness and height by approximately one third to one half of the thickness of the pre-existing jaw bone. The top surface of the resultant model is rounded so that a cross section of the model has a convex upper surface and a concave lower surface that conforms to the shape of the jaw bone (See FIG. 5). The ends of the resultant model are tapered as shown in FIG. 4.

The model is then used to make a Citricon split mold, having the parting line midway between the top and bottom surfaces.

The bottom part of the mold is filled with HEMA-wetted coarse PMMA particles and heated dielectrically for a sufficient time (about two minutes) to weld the particles together. The top half of the mold is filled with HEMA-wetted PMMA fine particles, and the bottom filled mold is placed over the top mold so that the fine particles are pressed against the coarse particle molding. The combined, closed mold is then heated dielectrically for four to six minutes.

Figure 5:
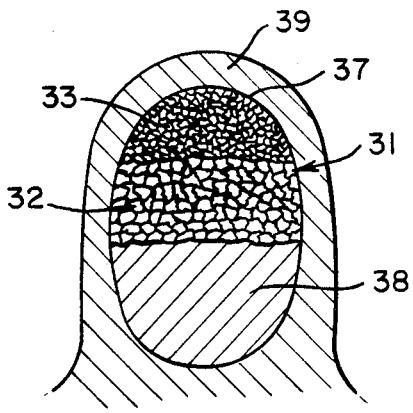
FIG. 5 is a cross section of the jaw bone implant taken along line 5—5 of FIG. 4.

The sintered molding is then cooled and removed from the mold and placed in boiling water for two minutes. The molding thus treated is then placed over the deteriorated jaw bone so that it fits perfectly, and the gums is closed over the implant. Referring to FIGS. 4 and 5 the coarse particle side 32, being in contact with the jaw bone 38, promotes bone attachment, while the fine particle side 33, being in contact with gum tissue 39, promotes gum attachment. After about 6 weeks of healing and attachment, dentures may be fitted.

Referring to FIG. 4A, an implant 41 for a jawbone 48 which has undergone much more extensive deterioration in a direction along the jawbone is shown. A region of coarse porosity 42 interfaces with jawbone 48, and a region of fine porosity 43 interfaces with gum tissue 47. Implant 41 can be produced following the procedure outlined above in Example 4. It is necessary to expose a longer segment of jawbone than would be necessary to produce the implant of FIG. 4. Ridges can be formed along surface 49 to enhance denture fit.

In those cases where some teeth or tooth roots remain to be extracted prior to fitting for a denture, it is advantageous to use the procedure as described in Example 1. The implanted porous roots are completely covered by the gum because no post is needed and after about 6 weeks, dentures can be fitted. This use of the freshly formed root sockets prevents bone recession and results in a better fitting denture, that will not slide or rock.

Modifications of Example 4 can be used to produce implants which serve as edentulous ridges when bone and gum tissue ingrowth result in attachment to an existing jawbone.

Various modifications of the invention in addition to those shown and described herein will become apparent to those skilled in the art from the foregoing description and accompanying drawing.

We claim:

1. A process for producing a porous implantable oral prosthesis comprising the steps of:
   (a) filling a portion of a mold cavity of the desired shape with relatively coarse polymeric particles coated with a hydrophilic monomer where said prosthesis is intended to interface with bone tissue;
   (b) filling the remainder of said mold cavity with relatively fine polymeric particles coated with a hydrophilic monomer where said prosthesis is intended to interface with soft tissue;
   (c) sintering the polymeric particles and polymerizing the hydrophilic monomer in the mold by the application of heat to form the prosthesis;
   (d) allowing the mold to cool;
   (e) removing the sintered prosthesis from the mold; and
   (f) placing the prosthesis in a hot liquid to remove toxic residues.

2. A process for producing a porous, implantable tooth root comprising the steps of:
   (a) cleaning an extracted tooth;
   (b) producing a mold with a cavity shaped to conform to the extracted tooth root;
   (c) filling a portion of said mold cavity with relatively coarse polymeric particles coated with a hydrophilic monomer where said prosthesis is intended to interface with bone tissue;
   (d) filling the remainder of said mold cavity with relatively fine polymeric particles coated with a hydrophilic monomer where said prosthesis is intended to interface with soft tissue;
   (e) sintering the polymeric particles and polymerizing the hydrophilic monomer in the mold by the application of heat to form the tooth root;
   (f) allowing the mold to cool;
   (g) removing the sintered tooth root from the mold; and
   (h) placing the tooth root in a hot liquid to remove toxic residues.

3. The process of claim 2 comprising the additional step of placing the cleaned extracted tooth in molten wax to form a thin conformal coating on said tooth before producing said mold.

4. A process for producing an implantable tooth having a porous root and a solid crown comprising the steps of:
   (a) cleaning an extracted tooth;
   (b) producing a first mold with a cavity shaped to conform to the extracted tooth root;
   (c) forming a second mold with a cavity in the shape of the crown portion of the extracted tooth protruding from said first mold;
   (d) removing the extracted tooth from the molds;
   (e) filling a portion of said first mold cavity with relatively coarse polymeric particles coated with a hydrophilic monomer where the root is intended to interface with bone tissue;
   (f) filling the remainder of said first mold with relatively fine polymeric particles coated with a hydrophilic monomer where the root is intended to interface with soft tissue;

(g) sintering the polymeric particles and polymerizing the hydrophilic monomer in the first mold by the application of heat;

(h) allowing the first mold to cool;

(i) filling the cavity of the second mold with a polymerizable liquid;

(j) placing the first mold over the second mold in proper alignment for the cavities to form a shape identical to the extracted tooth, and to allow a portion of said polymerizable liquid to penetrate said root;

(k) polymerizing the liquid;

(l) removing the tooth from the mold; and (m) placing the tooth in a hot liquid to remove toxic residue.

5. The process of claim 4 comprising the additional step of applying fluid pressure during the polymerization of said liquid.

6. The process of claim 4 comprising the additional step of inserting a reinforcing core member in said first mold cavity before sintering or immediately thereafter.

7. The process of claim 1 or 2 comprising the additional step of inserting an end of a temporary post comprised of a nonpolar plastic into said mold cavity before sintering.

8. The process of claims 1 or 2 comprising the additional step of inserting a reinforcing core member in said mold cavity before sintering.

9. A process for producing a porous implantable prosthesis comprising the steps of:
  (a) filling a portion of a mold cavity of the desired shape with relatively coarse polymeric particles coated with a hydrophilic monomer where said prosthesis is intended to interface with bone tissue;
  (b) filling the remainder of said mold cavity with relatively fine polymeric particles coated with a hydrophilic monomer where said prosthesis is intended to interface with soft tissue;
  (c) sintering the polymeric particles and polymerizing the hydrophilic monomer in the mold by the application of heat to form the prosthesis;
  (d) allowing the mold to cool;
  (e) removing the sintered prosthesis from the mold; and
  (f) placing the prosthesis in a hot liquid to remove toxic residues.

10. The process of claims 1, 2, 4, or 9 in which the step of sintering the polymeric particles and polymerizing the hydrophilic monomer is carried on at atmospheric pressure.

11. The process of claims 1, 2, 4, or 9 in which the polymeric particles are comprised of polymethylmethacrylate.

12. The process of claims 1, 2, 4, or 9 in which the sintering is performed by heating in a dielectric oven.

13. The process of claims 1, 2, 4, or 9 in which the sintering is performed at a temperature in the range of from about 175° C. to about 225° C.

14. The process of claims 1, 2, 4, or 9 in which the hot liquid is boiling water.

15. The process of claims 1, 2, 4, and 9 in which the hydrophilic monomer is hydroxyethyl methacrylate.

16. The process of claims 1, 2, 4, or 9 in which the hydrophilic monomer is combined with a crosslinking agent comprising one tenth percent to five percent by weight of the monomer.

17. The process of claims 1, 2, 4, or 9 in which the hydrophilic monomer is hydroxyethyl methacrylate combined with a crosslinking agent comprising one tenth percent of five percent by weight of the monomer.

18. The process of claim 17 in which the crosslinking agent is methacrylic diester of ethylene glycol.

19. The process of claim 18 in which the methacrylic diester of ethylene glycol is selected from the group consisting of:
  (a) tetraethyleneglycol dimethacrylate,
  (b) triethyleneglycol dimethacrylate,
  (c) diethyleneglycol dimethacrylate,
  (d) monoethyleneglycol dimethacrylate, and
  (e) mixtures thereof.

* * * * *